US006764769B2

United States Patent
Kotte et al.

(10) Patent No.: US 6,764,769 B2
(45) Date of Patent: Jul. 20, 2004

(54) APATITE-COATED METALLIC MATERIAL, PROCESS FOR ITS PREPARATION, AND ITS USE

(75) Inventors: Bernd Kotte, Dresden (DE); Jürgen Hofinger, Dresden (DE); Tanja Hebold, Dresden (DE)

(73) Assignee: Biomet Merck GmbH, Altdorf (CH)

( * ) Notice: Subject to any disclaimer, the term of this patent is extended or adjusted under 35 U.S.C. 154(b) by 106 days.

(21) Appl. No.: 10/162,691

(22) Filed: Jun. 6, 2002

(65) Prior Publication Data
US 2003/0031983 A1 Feb. 13, 2003

(30) Foreign Application Priority Data
Jun. 6, 2001 (DE) .......................................... 101 28 259

(51) Int. Cl.⁷ ............................ B32B 15/04; C25D 9/04
(52) U.S. Cl. ...................... 428/469; 205/137; 205/318; 205/320; 205/322; 428/702; 428/926
(58) Field of Search ................................. 428/469, 702, 428/926; 205/137, 318, 320, 322

(56) References Cited

U.S. PATENT DOCUMENTS

| 3,892,648 A | | 7/1975 | Phillips et al. |
| 5,413,693 A | * | 5/1995 | Redepenning ............. 205/318 |
| 5,458,863 A | | 10/1995 | Klassen |
| 5,723,038 A | | 3/1998 | Scharnweber et al. |

OTHER PUBLICATIONS

English Abstract of DE19504386, Mar. 3, 1998.

* cited by examiner

Primary Examiner—Robert R. Koehler
(74) Attorney, Agent, or Firm—Millen, White, Zelano, Branigan, P.C.

(57) ABSTRACT

The invention relates to a novel apatite-coated metallic material having improved surface quality and biocompatibility, a process for its preparation, and the use of the material for bone implants, in particular dental implants, artificial joints and fixative material for accident surgery (osteosynthesis material). The coating in this case consists of a thick covering of hydroxyapatite crystals and/or amorphous calcium phosphate spheres having a specific surface area of less than 15 $m^2/g$.

15 Claims, No Drawings

APATITE-COATED METALLIC MATERIAL, PROCESS FOR ITS PREPARATION, AND ITS USE

The invention relates to a novel apatite-coated metallic material having improved surface quality and biocompatibility, a process for its preparation, and the use of the material for bone implants, in particular dental implants, artificial joints and fixative material for accident surgery (osteosynthesis material).

It is known that coated implants integrate better with calcium phosphate, in particular with the bone mineral hydroxyapatite (HAP ($Ca_{10}(PO_4)6OH$)). Different processes are used for coating implants with calcium phosphate, such as, for example, plasma injection, sol-gel processes, electrophoresis, and electrochemically assisted deposition.

Electrochemically assisted deposition has advantages compared with other processes on account of the possibility of the production of uniform (even with very rough surfaces) and thin layers, the possibility of the specific control of the phases to be deposited by means of electrical parameters, and produces lower costs in preparation.

In electrochemically assisted deposition, calcium phosphate precipitates on the cathode, which forms the implant. The resulting layer is very porous and can therefore be removed easily from the surface. There are various possibilities for decreasing the porosity.

According to U.S. Pat. No. 3,892,648, an emulsion of bone powder and collagen is applied electrochemically to the metallic implant and a stronger adhesion is achieved therewith by means of the collagen.

In DE 19504386 A1, the deposited calcium phosphate layer is combined in graded form with the metal surface. Calcium phosphate crystals are surrounded by a growing oxide layer. A disadvantage of this process is: it functions only with implants of titanium or titanium alloys. The porosity of the coating is not lowered and the mechanical properties are thus not improved.

In the patent U.S. Pat. No. 5,458,863, using an electrochemically assisted deposition, a brushite layer is first produced, which is then converted to hydroxyapatite at temperatures between 20 and 100° C. The adhesion between layer and substrate is improved by regular removal of gas bubbles on the substrate surface during the coating. It is disadvantageous in this process that the conversion process lasts about 36 hours. At temperatures of 750° C., according to WO 9813539, hydroxyapatite crystals are formed from the electrochemically assisted deposition of a calcium phosphate phase and the adhesion is improved. Here, the higher temperatures are especially to be mentioned as particularly disadvantageous. In the patent U.S. Pat. No. 5,205,921, after the electrolytic deposition the adhesion of the layer produced is improved by means of ultrasonic processes in a methanol bath. The method is based on the fact that crystallites having low adhesion to the substrate are detached again by the influence of ultrasound.

There is still a great need for implant materials having an improved surface and compatibility with the biological system.

An object of the invention is therefore an apatite-coated metallic material having decreased porosity and improved adhesion. Upon further study of the specification and appended claims, further objects and advantages of this invention will become apparent to those skilled in the art.

According to the invention, these objects are achieved by means of an apatite-coated metallic material, in which the coating consists of a thick covering of hydroxyapatite crystals preferably having a needle length (see, e.g., Racquel Z. LeGeros, Calcium Phosphates in Oral Biology and Medicine (1991) p. 20) in the range from 200 to 300 nm and/or amorphous calcium phosphate spheres preferably having a diameter in the range from 35 to 200 nm with the total coating having a layer thickness preferably of >1 $\mu$m particularly from 2 to 5 $\mu$m, and the coating has a specific surface area of less than 15 $m^2/g$.

Examples of the metallic material to be coated include titanium or titanium alloys, CoCrMo alloys or stainless steels.

According to the invention, the novel apatite-coating material is dissolved by means of an electrochemically assisted process using a substrate electrode formed from the metallic material and a counterelectrode in which, as electrolyte, an aqueous solution containing calcium and phosphate ions is used.

According to the invention, the coating is carried out by cathodic polarization in a number of successive process cycles. A process cycle consists of cathodic polarization in one or more successive steps with identical or different high constant current densities, and a rinsing and/or drying phase following thereon.

The concentration ratio of calcium and phosphate ions in the electrolyte preferably corresponds substantially to that of hydroxyapatite.

By means of one embodiment of the process according to the invention, a decrease in the porosity takes place in that the process is repeated two or more times in a number of cycles with electrochemical calcium phosphate deposition and subsequent rinsing and/or drying.

Electrochemically, hydroxyapatite (HAP) or its precursors (amorphous calcium phosphate (ACP)/mixed states of ACP/HAP) are deposited on the metallic material. The needle length size of the hydroxyapatite crystals is preferably between 200 and 300 nm. The amorphous spheres can be varied in their diameter, preferably in the range from 35 to 200 nm. The compressed layers are preferably achieved by an exchange between short coating phases and rinsing and/or drying phases following thereon. The drying is carried out at room temperature. During the drying, the used electrolyte liquid is stripped off the porous layers. On the next immersion, the cavities fill with fresh electrolyte liquid. An electrochemically assisted deposition of calcium phosphate phases thus also takes place in the cavities. Moreover, the metallic material body is preferably moved continuously during the coating and drying phases in order to obtain a uniform coating, even with specially shaped material bodies and very rough/porous surfaces.

In one embodiment of the process according to invention, the cathodic polarization takes place at a constant current density of 0.5 $mA/cm^2$ to 20 $mA/cm^2$ or in the individual process cycles at different current densities, the current density being decreased in the subsequent cycles.

The invention also comprises the use of the novel apatite-coated metallic materials for the production of implants, in particular dental and joint implants, and material for the stabilization of the bone in fractures (osteosynthesis material).

The entire disclosure[s] of all applications, patents and publications, cited above or below, and of corresponding German Application No. 10128259.1, filed Jun. 6, 2001, is hereby incorporated by reference.

EXAMPLES

In the foregoing and in the following examples, all temperatures are set forth uncorrected in degrees Celsius; and, unless otherwise indicated, all parts and percentages are by weight.

Working Example 1

Coating sample: Cylinder of titanium alloy (TiAl$_6$V$_4$), 10 mm diameter, 46 mm long, ground with SIC paper, 1200 grit.

This sample was cleaned in ethanol using ultrasound before coating, rinsed off with deionized water, dried by means of a stream of air, then covered on both ends with a holder including a contact device of Deguform silicone material. The area to be coated was 6.28 cm$^2$.

The electrolyte liquid was prepared from 5 liters of deionized water with 2.455 g of CaCl$_2$.2H$_2$O and 1.15 g of NH$_4$H$_2$PO$_4$ introduced, which corresponds to a Ca/P ratio of 1.67. The temperature of the electrolyte liquid which was controlled by means of a thermostat was 37° C. The pH was adjusted to 6.45 using an NH$_4$OH solution.

The sample is polarized as a cathode; platinum gauze electrodes were used as the anode. The coating took place in 10 cycles. One cycle comprised:

Cathodic polarization for five minutes with a constant current of 63 mA, then rinsing for 1 minute in deionized water and then drying for 5 minutes with a fan.

Results:

A scanning electron micrograph of the apatite coating obtained according to Working example 1 on TiAl$_6$V$_4$ shows, macroscopically, the layer appearing to be uniformly white and adhereing well. The investigation on the scanning electron micrograph shows a closed layer with apatite-like needles of about 200–300 nm length. The energy-dispersive X-ray analysis shows a Ca/P ratio of 1.67, which corresponds to hydroxyapatite. The BET analysis according to DIN 66131 shows a specific surface area of 9.25 square meters per gram. In comparison to this, in the case of a non-compressed deposition a specific surface area of about 60 square meters/gram is achieved. By means of etching and skew analysis in the scanning electron micrograph, the layer thickness was measured as about 1.8 μm.

An IR-spectroscopic analysis (FTIR) confirms that the coating is hydroxyapatite. The IR spectra of hydroxyapatite powders from Merck and of the coated sample have identical absorption bands.

A scanning electron micrograph of the apatite coating obtained according to Working example 1 on TiAl$_6$V$_4$ which has been mechanically detached from the substrate surface shows, on the bottom of the coating (substrate side), an area of high density, which decreases in the layer surface direction.

Working Example 2

Identical sample size, coating and results as in Working example 1. However, the sample material is the alloy CoCr$_{28}$Mo.

Working Example 3

Identical sample size, coating as in Working example 1. However, within the process cycles the polarization was carried out in two stages with the following current densities:

1 minute at 75 mA, 4 minutes at 50 mA.

Results: needle length about 200–300 nm, even tighter packing; i.e. lower specific surface.

Working Example 4

Identical sample size, coating as in Working example 1. However, in the course of the 5-minute cathodic polarization, the current was altered as follows in cycles 1, 3 and 8: 1 min at 63 mA, 4 min at 5.6 mA. In cycles 2, 4, 5, 6, 7, 9, 10, the current was 5.6 mA.

A scanning electron micrograph of the coating obtained according to Working example 3 shows, macroscopically, the layer appearing uniformly white and adhering well. The investigation in the scanning electron micrograph shows a closed layer with calcium phosphate spheres of about 50 to 150 nm diameter. By means of etching and skew analysis in the scanning electron micrograph, the layer thickness was measured as about 1.8 μm.

Working Example 5

Identical sample size, coating as in Working example 1, but in 25 cycles. A cycle comprises: 1-minute cathodic polarization at 63 mA, 1 min at 50 mA.

Result: mixing state (ACP spheres and HAP needles).

A scanning electron micrograph of the coating obtained according to Working example 5 shows, macroscopically, the coating appearing uniformly white and adhering well. The investigation in the scanning electron micrograph shows a closed layer with calcium phosphate spheres and hydroxyapatite needles.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. An apatite-coated metallic material, comprising a metallic material and a coating thereon comprising a thick covering of hydroxyapatite crystals and/or amorphous calcium phosphate spheres and the coating having a specific surface area of less than 15 m$^2$/g.

2. A material according to claim 1, wherein the metallic material consists of titanium or a titanium alloy, a CoCrMo alloy or a stainless steel.

3. A process for the preparation of an apatite-coated metallic material of claim 1 by an electrochemically assisted process using a substrate electrode formed from the metallic material and a counterelectrode in which, as electrolyte, an aqueous solution containing calcium and phosphate ions is used, wherein a cathodic polarization takes place in a number of successive process cycles, a process cycle of cathodic polarization comprising one or more successive stages having identical or different high constant current densities and a rinsing and/or drying phase following thereon.

4. A process according to claim 3, wherein the concentration ratio of calcium and phosphate ions in the electrolyte corresponds to that of hydroxyapatite.

5. A process according to claim 3, wherein the material is constantly turned during the process cycles.

6. A process according to claim 4, wherein the material is constantly turned during the process cycles.

7. A process according to claim 3, wherein the cathodic polarization is carried out at a constant current density of 0.5 mA/cm$^2$ to 20 mA/cm$^2$ or takes place in individual process cycles at different current densities, the current density being decreased in the subsequent cycles.

8. A process according to claim 4, wherein the cathodic polarization is carried out at a constant current density of 0.5 mA/cm² to 20 mA/cm² or takes place in individual process cycles at different current densities, the current density being decreased in the subsequent cycles.

9. A process according to claim 5, wherein the cathodic polarization is carried out at a constant current density of 0.5 mA/cm² to 20 mA/cm² or takes place in individual process cycles at different current densities, the current density being decreased in the subsequent cycles.

10. A bone implant, dental implant, artificial joint, osteosynthesis material or fixative material for accident surgery comprising an apatite-coated metallic material of claim 1.

11. A bone implant, dental implant, artificial joint, osteosynthesis material or fixative material for accident surgery comprising an apatite-coated metallic material of claim 2.

12. The material of claim 1, wherein the coating has a thickness of >1 μm to 5 μm.

13. The material of claim 1, wherein the coating comprises hydroxyapatite crystals having a needle length in range from 200 to 300 nm.

14. The material of claim 1, wherein the coating comprises amorphous calcium phosphate spheres having a diameter in the range from 35 to 200 nm.

15. The material of claim 1, wherein the coating has a thickness of 2 μm to 5 μm.

* * * * *